United States Patent
Lewis et al.

[11] Patent Number: 5,539,137
[45] Date of Patent: Jul. 23, 1996

[54] ARYL SUBSTITUTED SILICONE FLUIDS HAVING HIGH REFRACTIVE INDICES AND METHOD FOR MAKING

[75] Inventors: Larry N. Lewis, Scotia; Susan A. Nye, Feura Bush, both of N.Y.

[73] Assignee: General Electic Company, Waterford, N.Y.

[21] Appl. No.: 472,797

[22] Filed: Jun. 7, 1995

[51] Int. Cl.⁶ .................................................. C07F 7/08
[52] U.S. Cl. .......................... 556/450; 556/451; 556/453; 556/459; 556/460; 556/461
[58] Field of Search .................................. 556/450, 451, 556/453, 461, 460, 459

[56] References Cited

U.S. PATENT DOCUMENTS

| | | |
|---|---|---|
| 3,159,662 | 12/1964 | Ashby . |
| 3,775,452 | 11/1973 | Karstedt . |
| 4,079,070 | 3/1978 | Maass et al. ............................ 556/460 |
| 4,599,440 | 7/1986 | Watanabe et al. ...................... 556/460 |
| 5,041,594 | 8/1991 | Herzig ..................................... 556/450 |
| 5,304,667 | 4/1994 | Haeberle et al. .................. 556/451 X |
| 5,329,036 | 7/1994 | Dougherty et al. ..................... 556/453 |
| 5,412,055 | 5/1995 | Loo .................................... 556/460 X |

*Primary Examiner*—Paul F. Shaver

[57] ABSTRACT

A method is provided for making silicone fluids having a high refractive index by effecting a hydrosilylation reaction between an arylacetylene such as phenylacetylene and a silicon hydride substrate, such as a cyclic or linear hyridosiloxane in the presence of a platinum catalyst.

11 Claims, No Drawings

ARYL SUBSTITUTED SILICONE FLUIDS HAVING HIGH REFRACTIVE INDICES AND METHOD FOR MAKING

BACKGROUND OF THE INVENTION

The present invention relates to the synthesis of aryl substituted silicone fluids by the hydrosilylation of an aryl substituted acetylene, such as phenylacetylene or diphenylacetylene with a hydride-functionalized silicone fluid.

Silicones fluids having a high refractive index, such as about 1.50, are of interest to the hair care products industry. For example, in addition to providing good feel, wet combing, and low static, silicones having a high refractive index can offer a maximum amount of sheen to hair.

It is generally known to those skilled in the silicone art, that a convenient way to increase the refractive index of a polydiorganosiloxane fluid consisting essentially of chemically combined dialkylsiloxy units is to introduce into the polydiorganosiloxane backbone, a significant number of siloxy units having aryl radicals attached to silicon by carbon-silicon bonds.

Various techniques are available for introducing arylsiloxy units into organopolysiloxanes. One method is based on the use of a convenient source of arylsiloxy such as a polydiorganosiloxane having siloxy units with phenyl radicals attached to silicon by carbon-silicon linkages. However, experience has shown that diphenylsiloxane copolymers have a tendency to crystallize at high levels of diphenylsiloxane. The incorporation of aryl radicals, such as a styrl substituent, into a polydiorganosiloxane using a hydrosilylation reaction is also another alternative for increasing arylsilicon substitution.

As reported by L. N. Lewis et al. in Organometallics, 1991, 10,3750, arylacetylenes, such as phenylacetylene, can undergo facile hydrosilylation with monomeric silylhydrides. Diphenylacetylene has been shown by M. Tanaka et al. Bull. Soc. Fr. 1992, 129, 667.b, to undergo dehydrogenative double silylation with a bis(hydrosilane) to give a cyclic unsaturated compounds as the major product.

Additional procedures are constantly being evaluated for providing silicone fluids having high indices of refraction.

SUMMARY OF THE INVENTION

The present invention is based on the discovery that aryl substituted silicone fluids having high indices of refraction and a viscosity in the range of 100 to 40,000 centipoise at 25° C., and preferably 1 00 to 20,000 at 25° C., can be made by the hydrosilylation of arylacetylenes. Arylacetylenes having the formula,

R-C≡C-R¹, (1)

where R is a $C_{(6-13)}$ monovalent aryl radical, and $R^1$ is hydrogen or an R radical, can be hydrosilylated with a member selected from the group consisting of, (a) a linear hydridosiloxane which consists essentially of at least one terminal unit of the formula,

$R^2(R^3)_2 SiO_{1/2}$, (2)

where $R^2$ is a monovalent radical selected from the group of hydrogen and a $C_{(1-13)}$ monovalent organic radical, and $R^3$ is a $C_{(1-13)}$ monovalent organic radical, and from 1 to 100 chemically combined disiloxy units selected from the group consisting of organohydridosiloxy units,

$H(R^3) SiO$, (3)

and, a mixture of such organohydridosiloxy, and diorganosiloxy units,

$(R^3)_2 SiO$, (4)

and, (b) a (3-8) cyclic hydridosiloxane consisting essentially of a member selected from the group consisting of the organohydridosiloxy units of (a) and a mixture of such organohydridosiloxy units and the diorganosiloxy units of (a).

In a further aspect of the present invention, it also has been found that the aryl substituted silicone fluids include aryl substituted silicone fluids having a conjugated aryl group either in the form of a styryl or styrenyl group, in instances where $R^1$ in formula 1 is hydrogen, and a diaryl group, such as a stilbene group, where $R^1$ in formula 1 is R. Surprisingly, the presence of such conjugated groups, has been found to enhance the refractive index of such silicone fluids.

STATEMENT OF THE INVENTION

There is provided by the present invention, an aryl substituted silicone fluid having a viscosity in the range of about 100 to about 40,000 centipoise at 25° C., and a refractive index of at least 1.5, comprising chemically combined diorganosiloxy units of the formula,

$QR^3 SiO$, (5)

where Q is a conjugated monovalent aryl radical selected from the group consisting of alkenyl substituted $C_{(6-13)}$monoaryl radicals, and alkenyl substituted $diC_{(6-13)}$aryl radicals, and $R^3$ is as previously defined.

In a further aspect of the present invention, there is provided a method for making an aryl substituted silicone fluid having a refractive index of at least 1.5, comprising effecting the hydrosilylation of an arylacetylene of formula (1), with a linear hydridosiloxane having from 1 to about 80 chemically combined disiloxy units selected from the group consisting of formulas 2 and 3, or 2 and a mixture of 3 and 4, or a (3-8) cyclic hydridosiloxane consisting essentially of chemically combined units of formula 3, or a mixture of 3 and 4.

DETAILED DESCRIPTION OF THE INVENTION

Radicals which are included within R of formula 1, are phenyl, tolyl, xylyl, and naphthyl, and preferably phenyl; haloaryl, such as chlorophenyl, alkoxy aryl such as methoxy phenyl, and nitro aryl are also included. In addition to hydrogen, radicals included within $R^2$, and organo radicals of $R^3$, are for example, $C_{(1-8)}$ alkyl radicals, such as methyl, ethyl, propyl, butyl and pentyl; haloalkyl for example trifluoropropyl; alkenyl radicals such as vinyl, and propenyl; cycloalkenyl, for example cyclohexenyl; $C_{(6-13)}$ aryl radicals such as phenyl, tolyl, xylyl, and naphthyl, and preferably phenyl, methoxyphenyl; haloaryl, such as chlorophenyl.

Preferably, the arylacetylenes of formula (1) are for example, phenylacetylene, diphenylacetylene, and the corresponding chloro, nitro, and methoxy derivatives. Additional arylacetylenes, such as arylacetylene compounds having substituents shown for R, are also included.

The linear hydridosiloxane having terminal units of formula (2), which consist essentially of disiloxy units shown by formulas (3) and (4), are preferably polydisiloxanes having terminal dimethylhydrogensiloxy units or trimethylsiloxy units, which linear hydridosiloxane can consists essentially of methylhydrogensiloxy units, or a mixture of methylhydrogensiloxy units and dimethylsiloxy units. These linear hydridosiloxanes preferably have from about 1 to about 80 disiloxy units and 0.2% to 1.6% of chemically combined hydrogen. The cyclic polydimethylsiloxanes are preferably cyclic trimer, tetramer and pentamer.

Experience has shown that in instances where diarylacetylene is used in the preparation of the aryl substituted silicone fluids of the present, solidification of the hydrosilylation product will likely occur, unless a $C_{(2-8)}$olefinic comonomer reactant, such as hexene, is concurrently used during the hydrosilylation step.

Although the aryl substituted silicone fluids can have a viscosity in the range of about 100 to about 20,000 centipoise at 25° C., depending on such factors as the nature of the substituents attached to silicon in the polydiorganosiloxane backbone, the linear length or cyclic size of the silicon hydride fluid used in the preparation of the fluid, the viscosities of the respective fluids can vary widely. For example, in instances where the fluid backbone is linear and substituted with hexane groups and phenylacetylene, or diphenylacetylene groups, a viscosity of about 100 to about 32,000 centipoise at 25° C. is not unusual.

Depending upon the nature of the reactants, the aryl substituted silicone fluids can be made by the hydrosilylation of arylacetylene with the hydridosiloxane fluid, or by the hydrosilylation of hydrolyzable silanes followed by cohydrolysis with appropriate diorganosilanes, such as dimethyldichlorosilane. In instances where hydrosilylation is used, platinum group metal catalyst, such as chloroplatinic acid, finely divided platinum metal, and platinum catalyst shown by Ashby, U.S. Pat. No. 3,159,601 and Karstedt, U.S. Pat. No. 3,775,452. An effective amount of platinum catalyst is 5 ppm to 200 ppm of Pt based on the weight of the hydrosilylation mixture. A temperature in the range of 25° C. to 150° C. can be used. An inert organic solvent is optional. Suitable inert solvents are cyclohexane, 2-propanol, toluene, hexane and heptane.

In order that those skilled in the art will be better able to practice the present invention, the following examples are given by way of illustration and not by way of limitation. All parts are by weight unless otherwise indicated.

EXAMPLE 1

A mixture of 85.45g (0.838 mol) of phenylacetylene, 12.36 g (0.147 mol) of 1-hexene, 70.74 g (0.93 mol Si-H) of a poly(methylhydrido)siloxane fluid having terminal trimethylsiloxy units and having an average of about 10 methyhydridosiloxy units, and sufficient platinum catalyst shown by Karstedt, U.S. Pat. No. 3,775,452, to provide 36 ppm of Pt catalyst based on acetylene, was heated with stirring to 60° C. for one hour and 75° C. for two hours. After stripping excess hexene, there was obtained 162 g of an orange, clear fluid. It had a viscosity of 5915 cSt, and a R.I. of 1.5465; GPC analysis showed a Mw of 3190 and Mn of 1680. Based on method of preparation, the product was a phenyl silicone fluid and useful as a hair product component.

EXAMPLE 2

A procedure similar to example 1 was performed, except that a poly(methylhydrido)siloxane fluid was used having 3.79 mol of Si-H and an average of about 80 methyhydridosiloxy units, 450 g of phenylacetylene, 280 g of a solvent in the form of a mixture of $C_{12}$ branched alkanes. The mixture was heated at 8 hours at 75° C., and at 80° C. for 2 additional hours using a total of 99 ppm of Pt catalyst. There was obtained 60 g of an orange, slightly hazy fluid having a viscosity of 32,000 centipoise and an R.I. of 1.5720.

EXAMPLE 3

There was added over a period of one hour, 4.76 g (79.3 mol of Si-H) of tetramethylcyclotetrasiloxane to a stirred mixture heated to 60° C. of 8.39 g (82.3 mol) of phenyl acetylene, 6 g of cyclohexane, and 40 ppm of Pt based on acetylene. The mixture was then heated for one hour to 75° C. The mixture was then stripped of volatiles at 50° C. under reduced pressure. There was obtained 12.0 g of an orange, slightly hazy fluid having a viscosity of 1000 cSt and an R.I. of 1.5745. The fluid was a phenyl silicone useful as a component in a hair preparation.

EXAMPLE 4

A procedure similar to example 2 was carried out, except that there was added over a period of one hour, 231g (3.79 tool Sill) of a linear hydridosiloxane having an average of about 15 methylhydridosiloxy units and terminal hydridodimethylsiloxy units to a mixture at 55° C. of 450 g of phenylacetylene, 280 g of a mixture of $C_{12}$ branched alkanes as a solvent, and 250 ppm of Pt. The reaction mixture was heated at 75° C. for 15 hours and then heated an additional five hours at 80° C. in the presence of an additional 39 ppm of Pt. Vacuum distillation at 75° C. provided an orange, slightly hazy fluid having a viscosity of 6000 centipoise at 25° C. and an R.I. of 1.5745.

EXAMPLE 5

There was added 3.42 g (19 mmol) of diphenyl acetylene dissolved in 2-3 g of toluene to a mixture stirring for one hour at 80° C. consisting of 0.41 g (4.9 mmol) of 1-hexene, 2.42 g (24.0 meq Si-H) of a poly(methylhydrido)siloxane fluid having terminal trimethylsiloxy units and an average of about 4 methyhydridosiloxy units and 70 ppm Pt based on acetylene. After an additional one hour at 80° C., the mixture was stripped of volatiles at 100° C. to provide 5.1g of a pale yellow fluid having an R.I. of 1.5615.

EXAMPLE 6

A procedure substantially similar to example 5 was carried out, except that 1.62 g (24.2 meq Si-H) of tetramethyldisiloxane was substituted as the poly(methylhydrido)siloxane fluid and a 50:50 mole of diphenylacetylene to hexene. There was obtained, 3.94 g of a pale yellow fluid having an R.I. of 1.5275.

EXAMPLE 7

There was added over a period of one-half hour, 16.1 g (0.14 mol) of dichloromethylsilane to a stirring refluxing mixture of 25.0 g (0.14 mol) of diphenyl acetylene, 200 ml of methane, and sufficient Pt catalyst to provide 220 ppm of Pt based on acetylene. After 17 hour, GC analysis showed complete conversion to product. The mixture was stripped of hexane. The residue was distilled at 121 ° C./0.2 torr to provide 36 g (88% yield) of a colorless liquid. Based on method of preparation, the product was 1-phenyl-1-(dichloromethylsilyl)-2-phenyl ethylene.

A mixture of 25 g (0.085 mol) of 1-phenyl-1-(dichloromethylsilyl)-2-phenyl ethylene and 11.0 g (0.085 mol) of dichlorodimethylsilane was added slowly to a solution cooled to °C. of 125 ml of water and 20 g of KOH. There was obtained a white solid. The solid was extracted into dichloromethane. The dichloromethane solution was washed with 10% HCl and water and dried with $MgSO_4$. The filtered organic layer provided 23.5 g of an aryl silicone fluid in the form of a viscous oil having an R.I. of 1.581.

We claim:

1. An aryl substituted silicone fluid having a viscosity in the range of about 100 to about 40,000 centipoise at 25° C., and a refractive index of at least 1.5, comprising chemically combined diorganosiloxy units of the formula, $QR^3SiO$, where Q is a conjugated monovalent aryl radical selected from the group consisting of alkenyl substituted $C_{(6-13)}$ monoaryl radicals, and alkenyl substituted di $C_{(6-13)}$ aryl radicals, and $R^3$ is a $C_{(1-13)}$ monovalent organic radical.

2. A polydiorganosiloxane fluid in accordance with claim 1, comprising chemical combined phenylstyrlmethylsiloxy units.

3. A polydiorganosiloxane fluid in accordance with claim 1, comprising chemically combined phenylstilbenemethylsiloxy units.

4. A cyclic polydiorganosiloxane fluid in accordance with claim 1.

5. A linear polydiorganosiloxane fluid in accordance with claim 1.

6. A polydiorganosiloxane fluid in accordance with claim 1, comprising a mixture of $QR^3SiO$ units and $(R^3)_2SiO$ units.

7. A method for making a polydiorganosiloxane fluid having a refractive index of at least 1.5, comprising effecting the hydrosilylation of an arylacetylene of the formula $R-C\ C-R^1$, with (A), a linear hydridosiloxane having from 10 to 80 chemically combined disiloxy units selected from the group consisting of, (i) a mixture of
  $R^2 (R^3)_2 SiO_{1/2}$, and
  $H(R^3) SiO$, and (ii) a mixture of
  $R^2 (R^3)_2 SiO_{1/2}$,
  $H (R^3) SiO$, and
  $(R^3)_2 SiO$, and (B) a (3-8) cyclic hydridosiloxane consisting essentially of chemically combined units of (iii),
  $H(R^3) SiO$, and (iv), a mixture of
  $H(R^3) SiO$, and
  $(R^3)_2 SiO$, in the presence of an effective amount of a platinum group metal catalyst, where R is a $C_{(6-13)}$ monovalent aryl radical, $R^1$ is hydrogen or an R radical, $R^2$ is a monovalent radical selected from the group of hydrogen and a $C_{(1-13)}$ monovalent organic radical, and $R^3$ is a $C_{(1-13)}$ monovalent organic radical.

8. A method in accordance with claim 7, where phenyl acetylene is reacted with a linear hydridosiloxane.

9. A method in accordance with claim 7, where phenyl acetylene is reacted with a cyclic hydridosiloxane.

10. A method in accordance with claim 7, where diphenylacetylene is reacted with a linear hydridosiloxane.

11. A method in accordance with claim 7, where diphenylacetylene is reacted with a cyclic hydridosiloxane.

* * * * *